United States Patent
Knittel et al.

(10) Patent No.: US 11,918,388 B2
(45) Date of Patent: Mar. 5, 2024

(54) STERILIZATION SIEVE TRAY WITH CORRUGATIONS OR INDENTED/BULGED SHEET METAL BASE

(71) Applicant: Aesculap AG, Tuttlingen (DE)

(72) Inventors: Timo Knittel, Wurmlingen (DE); Dennis Görz, Tuttlingen (DE); Bianca Rosin, Tuttlingen (DE); Eva Streit, Bodman-Ludwigshafen (DE)

(73) Assignee: Aesculap AG, Tuttlingen (DE)

( * ) Notice: Subject to any disclaimer, the term of this patent is extended or adjusted under 35 U.S.C. 154(b) by 785 days.

(21) Appl. No.: 16/978,226

(22) PCT Filed: Mar. 1, 2019

(86) PCT No.: PCT/EP2019/055181
§ 371 (c)(1),
(2) Date: Sep. 4, 2020

(87) PCT Pub. No.: WO2019/170550
PCT Pub. Date: Sep. 12, 2019

(65) Prior Publication Data
US 2021/0000560 A1    Jan. 7, 2021

(30) Foreign Application Priority Data
Mar. 5, 2018 (DE) .................. 10 2018 104 938.2

(51) Int. Cl.
*A61B 50/34* (2016.01)
*A61B 50/39* (2016.01)

(52) U.S. Cl.
CPC .............. *A61B 50/34* (2016.02); *A61B 50/39* (2016.02)

(58) Field of Classification Search
CPC ......... A61B 50/00; A61B 50/30; A61B 50/34; A61B 50/36; A61B 50/39; A61B 50/20; A61B 50/22
See application file for complete search history.

(56) References Cited

U.S. PATENT DOCUMENTS

| 5,183,643 A | 2/1993 | Nichols |
| 6,379,631 B1 | 4/2002 | Wu |

(Continued)

FOREIGN PATENT DOCUMENTS

| CN | 2848161 Y | 12/2006 |
| CN | 101947512 A | 1/2011 |

(Continued)

OTHER PUBLICATIONS

Office Action received in Chinese Application No. 201980017476.7 dated Sep. 28, 2021, with translation, 13 pages.

(Continued)

*Primary Examiner* — Sean E Conley
*Assistant Examiner* — Justin Hwang
(74) *Attorney, Agent, or Firm* — Christopher A. Rothe; Culhane Meadows PLLC

(57) ABSTRACT

A sieve tray for receiving objects to be disinfected or sterilized includes a base which has a plurality of openings and a base plane delimited by lateral walls. The base is a sheet metal part which has corrugations or indentations which protrude out of the base plane towards the sieve tray interior and/or sieve tray exterior such that the sheet metal part imitates a meshwork structure.

12 Claims, 4 Drawing Sheets

(56) References Cited

U.S. PATENT DOCUMENTS

Figure 1:
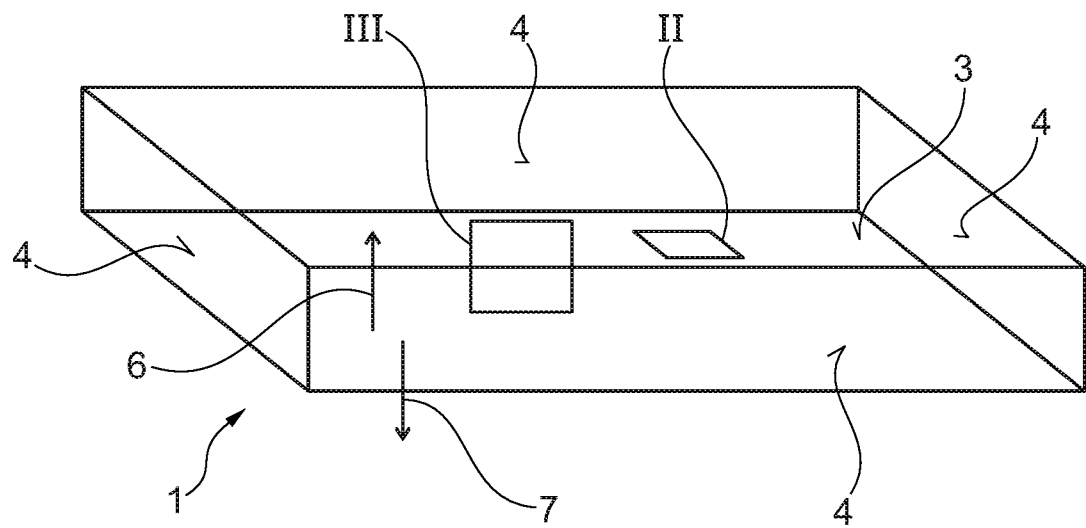

| | | | |
|---|---|---|---|
| 10,456,484 B2 | 10/2019 | Kemp et al. | |
| 2005/0163686 A1* | 7/2005 | Bettenhausen | ........... A61L 2/26 |
| | | | 206/370 |

FOREIGN PATENT DOCUMENTS

| | | | | |
|---|---|---|---|---|
| CN | 202897009 U | 4/2013 | | |
| CN | 106999616 A | 8/2017 | | |
| CN | 107335612 A | 11/2017 | | |
| DE | 10124253 A1 * | 12/2002 | ............. | A61B 50/20 |
| DE | 10124253 A1 | 12/2002 | | |
| DE | 202006011942 U1 | 10/2006 | | |
| DE | 102008055021 A1 | 6/2010 | | |
| DE | 102010050919 A1 | 5/2012 | | |
| DE | 102013002458 A1 | 8/2014 | | |

OTHER PUBLICATIONS

Search Report received in Chinese Application No. 201980017476.7 dated Sep. 23, 2021, with translation, 5 pages.
Office Action received in Chinese Application No. 201980017476.7 dated Mar. 2, 2022, with translation, 19 pages.
German Search Report received in Application No. 10 2018 104 938.2 dated Oct. 23, 2018, 11 pages, with translation.
International Search Report received in Application No. PCT/EP2019/055181 dated May 17, 2019, 2 pages, with translation.

* cited by examiner

STERILIZATION SIEVE TRAY WITH CORRUGATIONS OR INDENTED/BULGED SHEET METAL BASE

CROSS-REFERENCE TO RELATED APPLICATION(S)

This application is the United States national phase entry of International Application No. PCT/EP2019/055181, filed Mar. 1, 2019, which claims the benefit of priority of German Application No. 10 2018 104 938.2, filed Mar. 5, 2018. The contents of International Application No. PCT/EP2019/055181 and German Application No. 10 2018 104 938.2 are incorporated by reference herein in their entireties.

FIELD

The present invention relates to a sterilization sieve tray, also called sieve/screen basket, such as a sterilization or disinfection sieve basket. Generic sieve baskets are used to provide a portable receiving container in a cleaning and disinfection device (CDD) or autoclave in a processing unit for medical devices (PUMD) for a number of items to be disinfected or sterilized, such as surgical cutting or gripping instruments.

BACKGROUND

The primary function of a sieve basket is to hold several items in its sieve basket interior, so that they can be handled as a single unit during the cleaning process. Furthermore, when assembling the sieve basket, the stored items must be prevented from slipping or sliding—in the interests of compact loading of the sieve basket.

Furthermore, a sieve basket should have as few sections as possible or none at all in which cleaning liquid (i.e. water with additives) used during the cleaning process accumulates, so that the used cleaning liquid is drained/drips off the sieve basket as completely as possible after the cleaning process.

Finally, it is important to ensure that sieve baskets do not have any sections susceptible to breakage or cracking even after intensive use, during which they are exposed to impact and cutting loads, thus minimizing the risk of injury or cutting for an operator.

From DE 20 2006 011 942 U1, a sieve basket is known, which is adapted to accommodate items to be disinfected or sterilized. The sieve basket has a bottom, in particular a sheet metal base, which is provided with a plurality of apertures. The bottom has a base plane bounded by side walls.

This base plane is designed flat as a kind of perforated metal plate. In order to prevent the stored items from slipping or sliding, a mat is inserted into the sieve basket. This mat prevents the sieve basket from being drained efficiently so that even after the sieve basket has been removed from the CDD, residual water causes interfering moistening of various sieve basket areas, in particular of the sieve basket bottom.

The problem of interfering moistening of the sieve basket bottom still exists even if the mat is not inserted. The perforated but flat base plane of the basket bottom has the effect that a surface contact is formed between the items stored in the sieve basket and the bottom, corresponding to the remaining web widths between the plate holes, at which residual water accumulates under capillary action, which in turn promotes interfering moistening.

Another genre of sieve baskets of the prior art is designed as a wire mesh instead of a perforated metal plate. A wire mesh has a grooved base plane that prevents the stored items from slipping or sliding away. Furthermore, a wire mesh causes less surface contact, for example with a flat ground, and consequently less capillary action.

The disadvantage of sieve basket wire meshes is, however, that not only residual water but also dirt accumulates in the individual junctions of the meshwork. Furthermore, after a certain period of use, the individual wires in a wire mesh will inevitably break or become detached, which considerably increases the risk of injury posed by a sieve basket wire mesh.

Furthermore, in a sieve basket wire mesh, the wall perforation corresponds to the bottom perforation. If the wire mesh is woven sufficiently coarsely in order to prevent the stored items from slipping or sliding on the base plane, it has the disadvantage that the wall perforation is so wide that the stored items can project through it, which again increases the risk of injury and makes handling more difficult.

Thus, the sieve baskets from the prior art all have the disadvantage that even after removal from the CDD they still moisten other surfaces in a non-desirable way due to adhering residual water. Depending on their design, they also have the disadvantage of an increased risk of injury, the disadvantage of the stored items slipping or sliding away, and/or the disadvantage of pollution or accumulation of germs.

SUMMARY

In view of this prior art, the present invention is based on the object of eliminating or at least reducing the disadvantages of the prior art, and in particular to provide a sieve basket which is drained efficiently so that it does not cause (hardly) any interfering moistening of further surfaces (such as that of a packing table) after removal from the CDD. This object of efficient draining is to be solved without further disadvantages, such as an increased risk of injury to the user or the stored items slipping or sliding away.

It has been found that the formation or arrangement of spacer feet/knobs, for example on the outside/underside of a flat perforated plate processed to form a sieve basket bottom, may reduce the contact area between the sieve basket and a flat ground and thus could improve the overall drip-off behavior, but the production of such a special plate would be complex and expensive and thus uneconomic overall. In addition, the spacer feet/knobs would be distributed over the plate surface with a certain distance between each other, which could therefore possibly bend depending on the distance selected between two adjacent spacer feet/knobs. For these reasons, such a solution to the problem stated at the beginning has not proven to be effective.

The basic idea of the present invention now pursues the basic concept of simulating the spatial structure of a wire mesh in an initially planar perforated plate by deforming the webs extending (and crossing) between the plate holes at least partially or in sections in one or more directions different from their respective web-extension direction, whereby the deformed webs themselves at least partially define point-like contact areas, for example with a planar ground. This makes it possible to form/retrofit virtually any initially flat perforated plate with this additional capability, i.e. the provision of almost any selectable number of point-like contact areas in the form of correspondingly three-dimensionally extending plate webs between the plate holes, for example by subjecting the initially flat perforated plate to a corresponding deformation step.

The following additional advantages can be derived from this configuration of the sieve basket according to the invention:
- Surfaces with which the sieve basket comes into contact after being removed from the CDD are not moistened by the CDD or are considerably less moistened.
- Neither residual water nor dirt accumulates in the perforated bottom structure.
- The danger of pricking is eliminated by the absence of a wire mesh.
- The perforation geometry of the bottom can be (cost-effectively) designed independently of the side walls, so that they can be adapted to different requirements.
- The stored items can also be prevented from slipping or sliding off without inserting a (silicone) mat.

The object of the invention is thus a sieve basket for holding medical items/work equipment to be disinfected or sterilized (generally: to be cleaned), with a bottom (perforated plate bottom) comprising a plurality of apertures/perforations, which has a base plane bounded by side walls. A medical item is understood here to be an item which is used, for example, in surgery or a related medical field.

According to the invention, the bottom of the sieve basket has or consists of a sheet metal part which has, preferably periodic, three-dimensional corrugations or indentations, also dents or depressions, which project from the base plane towards the sieve basket interior/inwards and/or towards the sieve basket exterior/outwards, so that the sheet metal bottom has a surface in the manner of a (wire) meshwork. Thus, a sheet metal part imitates/simulates/reproduces or replicates a meshwork surface structure, whereby the structure of a meshwork and that of a perforated metal plate are synergistically combined with each other. Preferably, at least the sheet metal part or the perforated plate of the sieve basket bottom has a number of through holes (pores), which are circumferentially defined by overlapping/crossing webs and are spaced from each other according to the web width. In accordance with the invention, individual webs have deformations (bulges/teeth) in one or more directions different from their respective web-extension direction, in particular (alternately) in the direction of the outside and/or inside of the sieve basket, resulting in a rough/teethed bearing surface on the bottom outside and/or a rough/teethed bearing surface on the bottom inside.

In the context of this application, the term 'base plane' is understood to be a plate extending in two main directions in space with almost constant thickness/material strength of the sheet metal in a third sub-direction. The corrugations or indentations/bulges in the third sub-direction give the bottom or perforated plate of the bottom a three-dimensional, varying structure which differs from the flat plate with the constant plate thickness/plate strength. It is advantageous not to form the indentations/bulges in the macro range, i.e. to form a single indentation/bulge over a plurality/number of webs, but to provide the indentations/bulges in the micro range, i.e. to form the indentation/bulge, for example, substantially within/along the length of a respective web (preferably between two or three crossing points/nodes with the respective other webs) and/or at a respective selected junction (area within a number of junctions surrounding a single junction in a circular shape as the middle and thus contact point of directly surrounding junctions).

In other words, the invention can be functionally described in such a way that the sieve basket has a bottom made of sheet metal (perforated metal plate/perforated plate), which (by means of corresponding indentations/bulges) has/simulates the surface geometry and structure of a (wire) meshwork, but without being woven. Thus, the invention has the effect of realizing the advantages of a meshwork (bottom structure with contact and fixation surfaces, efficient dripping) without its disadvantages (see below). Weaving means that two interlaced strands/wires overlap/lie on top of each other in the junctions. For sieve baskets, such overlapping is associated with the considerable disadvantage that germs and dirt particles accumulate in the overlapping point, i.e. the junction, as these are difficult to reach and therefore difficult to clean. This disadvantage is efficiently eliminated by the 'meshwork simulation' according to the invention.

The inventive idea, therefore, is that the formation of a mesh-like perforated plate prevents the items to be cleaned from slipping away during the packing process of the sieve basket on the one hand, while on the other hand the presence of residual water in the sieve basket after the cleaning process in the CDD is reduced or even prevented, so that there is no interfering moistening (of the packing table, for example).

In an advantageous embodiment of the invention, the bottom is composed of a plurality of longitudinal strut pairs/longitudinal-web pairs and transverse strut pairs/transverse-web pairs, respectively running parallel in the base plane, which preferably run perpendicular (or at a different angle) to each other in the base plane, so that the bottom has a grid structure with, for example, rectangular apertures/holes. The strut pair/web pair is defined as two struts/webs of the sheet metal base lying side by side and running in the same direction. Since the bottom has corrugations or indentations/bulges, the apertures/holes preferably vary in the sieve basket height direction, which inhibits the capillary effect they normally produce, thus further promoting efficient draining.

In particular, if the apertures have a rectangular shape when viewed in the base plane and form a three-dimensional roof shape (or butterfly shape) consisting of two triangles, each of which is formed in a plane with opposing slopes, due to the corrugations or indentations/bulges to the sieve basket interior and/or sieve basket exterior, the capillary action coming from the apertures/holes is practically eliminated, which counteracts any interfering moistening of further surfaces. The (hypothetical) vertex of the roof shape (/butterfly shape) preferably runs between two diagonally arranged junctions of a grid structure of the bottom, as already explained above.

A further advantageous configuration is characterized by the fact that a respective pair of webs/struts is formed by two struts with a wave form to form the corrugations or indentations/bulges. In this configuration, each strut/web has (approximately) a sinusoidal shape, i.e. the form of a sine function, in order to ensure that the struts project into the sieve basket interior or project into the sieve basket exterior.

Advantageously, the waveforms of the two webs/struts of a web/strut pair run complementarily to each other in this configuration, so that at the longitudinal or transverse position (depending on whether it is a longitudinal or a transverse strut pair) at which one strut of the strut pair has a wave crest, the other strut of the strut pair has a wave trough (the sine waves of two adjacent, parallel webs/struts are thus shifted by $7r$), so that the corrugations or indentations/bulges are equally distributed over the entire bottom, preferably with the exception of a transition edge or frame section in the area of the side walls (i.e. at a transition area adjacent to the side walls). Alternatively, it may be provided that in this configuration, one strut of a strut pair (approximately) reflects the course of a sine function and the adjacent strut reflects the course of a cosine function, wherein the x-axis of those functions corresponds to the parallel strut pairs. In other words, one strut has a sinusoidal shape, while the adjacent strut of the pair of struts has a cosine shape or is phase-shifted by half a pi.

In a preferred embodiment of the invention, the preferably smooth, i.e. flat, side walls also have apertures/holes/pores, which, however, optionally differ in shape and size from the apertures/holes of the bottom. In particular the apertures/holes in the side walls are to be made smaller/more finely meshed than those of the bottom in order to prevent items stored in the sieve basket from projecting from the side walls and at the same time to enable efficient dripping through the (more coarsely meshed) bottom. The invention thus allows a flexible adaptation of the individual surfaces (bottom/side surfaces) to their respective (partial) functional area.

As soon as the individual struts/webs of the longitudinal strut pairs and the transverse strut pairs intersect in bottom nodes distributed in a grid-like manner in the base plane, wherein the sheet-metal material depth of a bottom node corresponds to the sheet-metal material depth of the remaining struts, the meshwork simulation deviates from a meshwork in the desired manner, in order not to include the disadvantage of a meshwork, namely the dirt-accumulating overlap at the junctions, in the meshwork simulation, so that the sheet metal base according to the invention simulates/imitates/images/projects the advantages of a meshwork without its disadvantages.

It is particularly advantageous here if some of the bottom nodes are arranged projecting towards the sieve basket interior/inwards and some of the bottom nodes are arranged projecting towards the sieve basket exterior/outwards. In this way, the sheet metal base forms point contacts both inwards and outwards, which do not develop a capillary effect that attracts residual liquid.

In this configuration, the bottom is further advantageously structured in such a way that a hypothetical connection line of the bottom nodes projecting towards the sieve basket interior runs diagonally to the grid structure (i.e. diagonally through the apertures arranged at right angles in the base plane) and is at right angles to a hypothetical connection line of the bottom nodes projecting towards the sieve basket exterior. This allows a uniform, area-wide configuration of the bottom, which efficiently holds the stored items in each bottom position and allows the bottom to drain satisfactorily with equal distribution.

In addition, an advantageous configuration of the sieve basket is distinguished by the fact that the three-dimensional bottom structure caused by the corrugations or indentations forms contact and fixation surfaces for items to be placed in the sieve basket, for example in the form of fluting, which increases the positional stability of the stored items. Therefore, no (silicone) mat needs to be placed on the bottom in order to ensure a secure, form-fit adhesion of the individual items.

BRIEF DESCRIPTION OF THE DRAWING FIGURES

Figure 2:
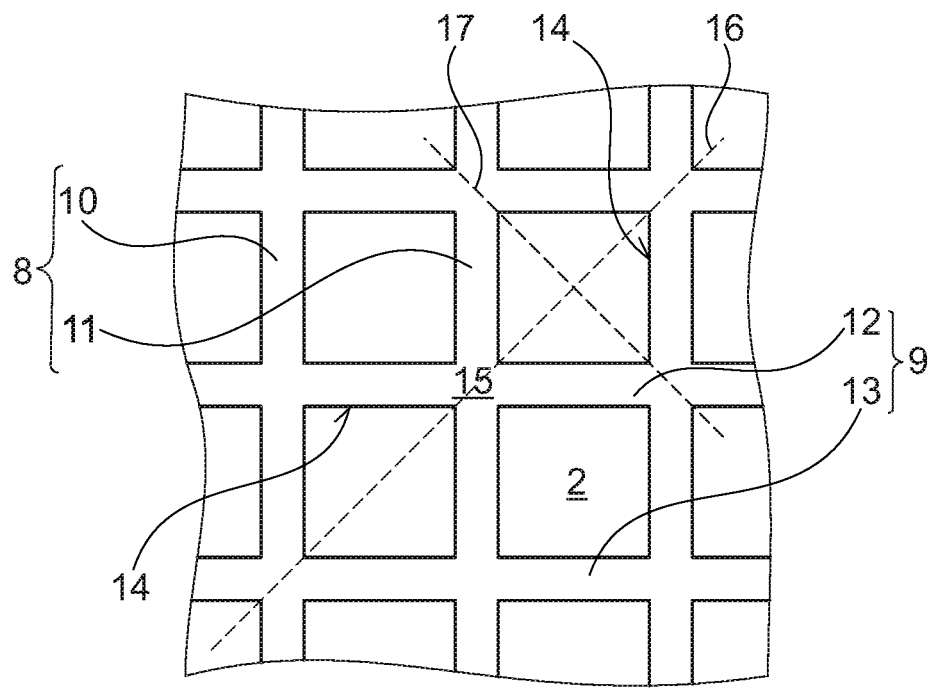
Figure 3:
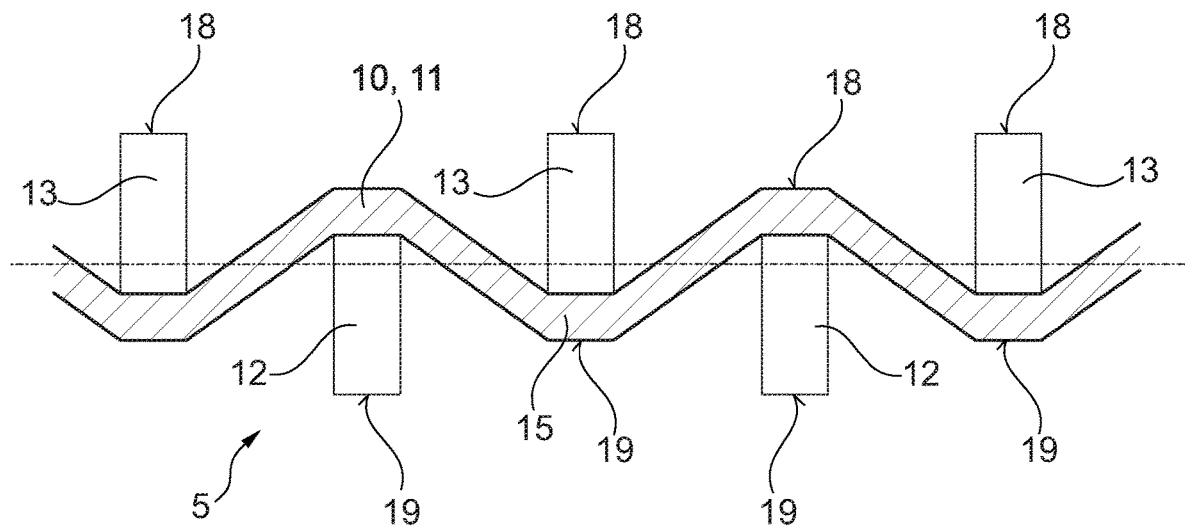
Figure 4:
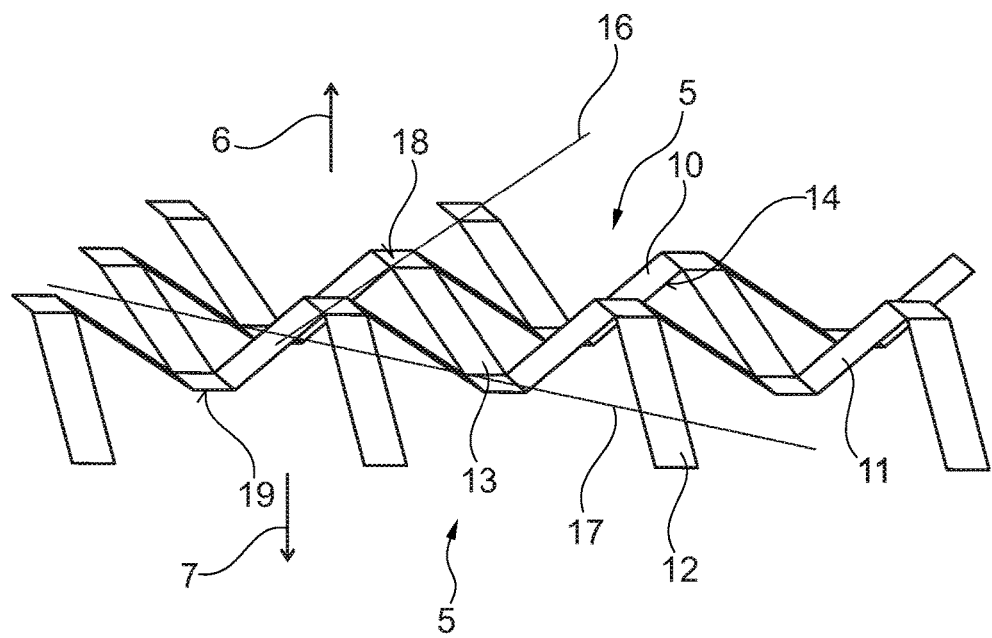
Figure 5:
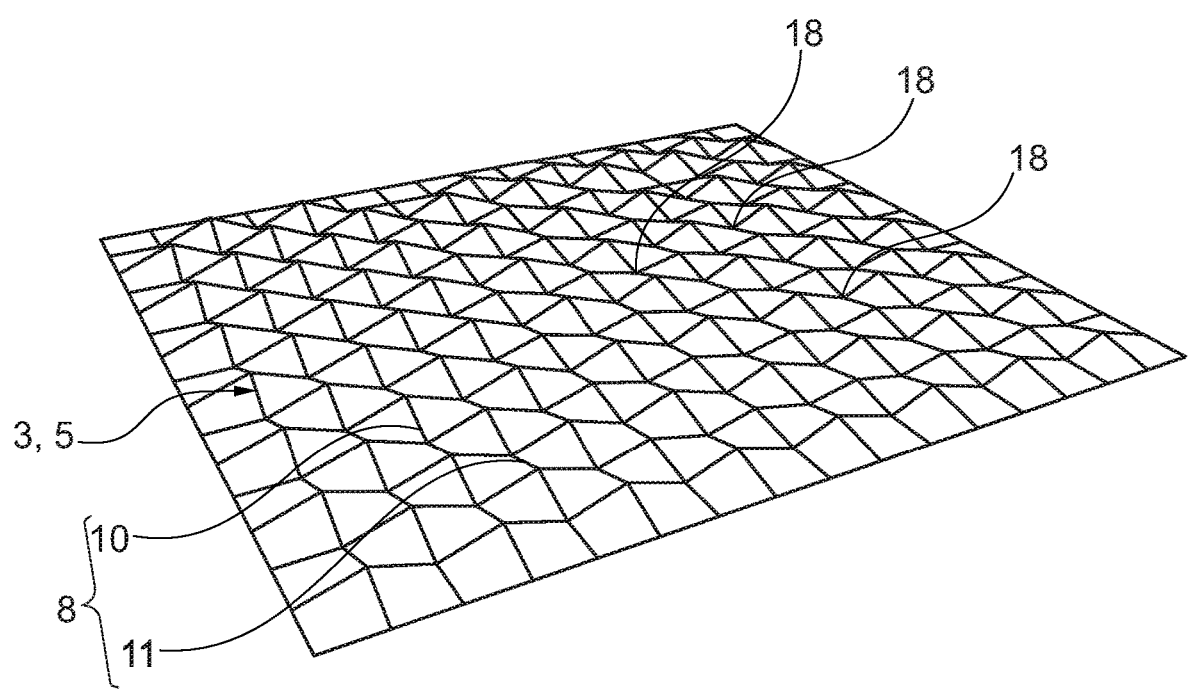
Figure 6:
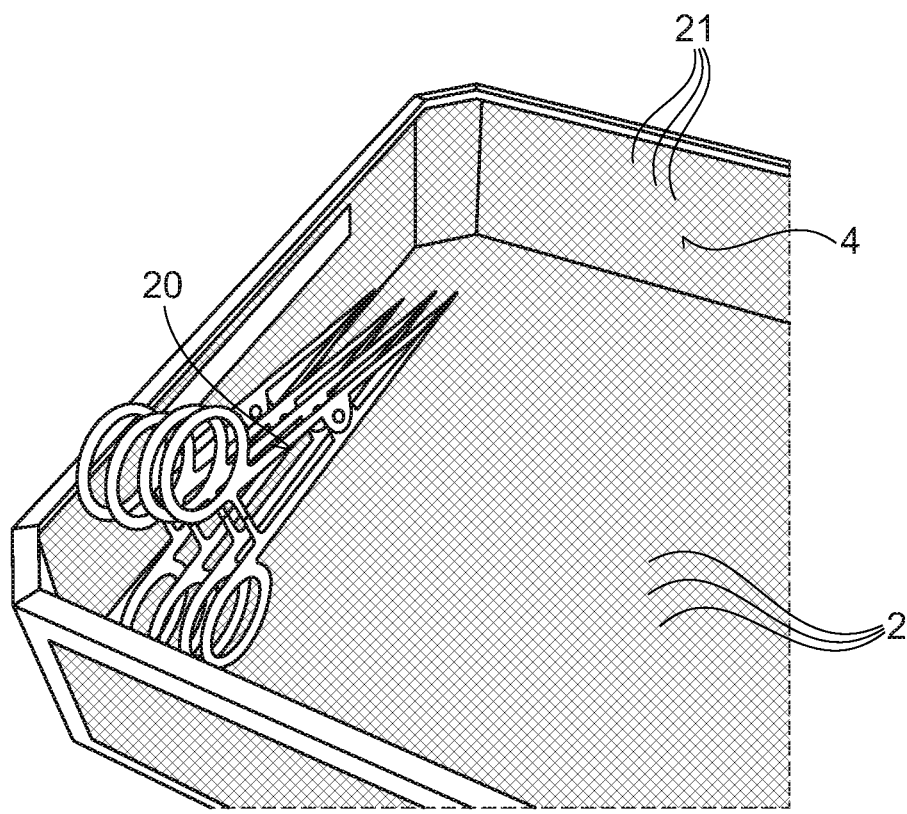

The invention is explained in more detail in the following on the basis of preferred embodiments with reference to the accompanying figures. The figures are merely schematic in nature and serve exclusively to understand the invention. The same elements are marked with the same reference signs. The figures show:

FIG. 1: shows a perspective view of a sieve basket;

FIG. 2: shows the area in FIG. 1 indicated by II schematically enlarged;

FIG. 3: shows the area in FIG. 1 indicated by III schematically enlarged;

FIG. 4: shows a perspective view of a meshwork-imitated bottom;

FIG. 5: shows a perspective view of a further configuration of the meshwork-imitated bottom; and FIG. 6: shows a section of the sieve basket with inserted items.

DETAILED DESCRIPTION

FIG. 1 shows a sieve basket 1 for holding items to be cleaned, having a plurality of apertures 2 as shown in the detailed view in FIG. 2. The sieve basket 1 has in the present case a rectangular base surface/base plane with a bottom 3 and side walls 4 extending from each side edge, i.e. four side walls 4 in the present case.

The bottom 3 is designed as a sheet metal part, which, as can be seen in the detailed view in FIG. 3, has periodic corrugations or indentations 5. These corrugations 5 project from the base plane towards the sieve basket interior 6 and in the present case also towards the sieve basket exterior 7, so that the sheet metal part/the bottom imitates a meshwork structure surface.

According to the detailed view in FIG. 2, which shows a top view of a section of the bottom 3, the bottom 3 has a grid structure in the projection. This is composed of a plurality of longitudinal strut pairs 8 (also called longitudinal-web pairs) and transverse strut pairs 9 (also called transverse-web pairs) running parallel in the base plane, i.e. in the present top view.

A single longitudinal strut pair 8 is composed of two longitudinal struts 10, 11. These longitudinal struts 10, 11 run parallel to each other in the base plane, i.e. in the present top view. A spatial view (cf. FIGS. 3 and 4) shows that each strut 10, 11 has a different, approximately complementary geometry in the third spatial direction, i.e. towards the sieve basket interior 6 and/or towards the sieve basket exterior 7.

A single transverse strut pair 9 is composed of two transverse struts 12, 13. These transverse struts 12, 13 run parallel to each other in the base plane, i.e. in the present top view. A spatial view (cf. FIGS. 3 and 4) shows that each strut 12, 13 has a different, approximately complementary geometry in the third spatial direction, i.e. towards the sieve basket interior 6 and/or towards the sieve basket exterior 7.

The surface spanned by the apertures 2 fulfils two different functions. Firstly, it provides a contact and fixation surface 14 on the edge surface of each strut 10 to 13 facing the aperture 2. This surface 14 increases with the size of the apertures 2. The larger the items to be inserted are, the larger the apertures 2 have to be designed in order to ensure that there is enough contact and fixation surface 14. Secondly, the surface spanned by the apertures 2 allows the cleaning liquid to drip out of the sieve basket 1. The drip-off function also increases with the size of the apertures 2. Accordingly, this second function also encourages the surface ratio between the strut pairs 8, 9 and the surface of the apertures 2 to be kept smaller than 1. A maximum is set for the surface area spanned by the apertures 2 in that it has to be small enough to prevent devices to be cleaned from falling out.

The grid structure defined by the bottom 3 has bottom nodes 15. According to the invention, these bottom nodes 15 do not lie in the same plane, because the corrugations 5 are formed. A particular advantage of the invention is that the bottom nodes 15, which are each formed by intersecting a longitudinal strut 10, 11 with a transverse strut 12, 13, have approximately the same material thickness as the respective longitudinal or transverse strut 10 to 13.

The meshwork simulation according to the invention not only allows the imitation of a meshwork, but also has the advantage over a meshwork that there is no overlap in the area of the node 15, i.e. no doubling of the material thickness, but there is the same constant material thickness as in the rest of the bottom. Before this feature is dealt with further in connection with FIG. 3, two further parameters of the present invention are introduced.

In this way, a part of the bottom nodes 15 can be hypothetically connected to each other to identify the first hypothetical connection line 16. As can be seen in the following, the bottom nodes 15 connected by the first hypothetical connection line 16 represent bottom nodes 15 which, in accordance with an advantageous configuration of the invention, are each arranged at the same height and project into the sieve basket interior 6. They each constitute, so to speak, a wave crest 18 (see FIG. 3) of the periodic corrugations 5.

In the base plane rotated by 90°, a second hypothetical connection line 17 can be seen next to line 16. This results from connecting the bottom nodes 15 left out by the first hypothetical connection line 16. As can be seen in the following, the bottom nodes 15 connected by the second hypothetical connection line 17 represent bottom nodes 15 which, in accordance with an advantageous configuration of the invention, are each arranged at the same height and project towards the sieve basket exterior 7. They each constitute, so to speak, a wave trough 19 (see FIG. 3) of the periodic corrugations 5.

These wave crests 18 and wave troughs 19 are shown in FIG. 3. FIG. 3 shows a sectional drawing through the bottom 3 (cf. section III of FIG. 1). The strut shown here is a longitudinal strut 10, 11 which, however, does not differ structurally from a transverse strut 12, 13 in its basic form. From the visible edges it can be seen that a first transverse strut 12 starts from each wave crest 18 of the longitudinal strut 10, 11, while a second transverse strut 13 starts from each wave trough 19. The reciprocity of the wave crest 18 and wave troughs 19 described above can be clearly seen here.

The longitudinal strut 10, 11 has an angular course in the present case. However, this shape is only of exemplary character. In other configurations, in particular an approximately sinusoidal waveform is desired.

FIG. 3 furthermore shows that the material thickness of the bottom node 15 does not exceed that of the remaining longitudinal strut 10, 11, which means that despite the meshwork simulation there is no disadvantageous overlapping of the struts as described above.

In FIG. 4, the corrugations 5 are shown in perspective. The first hypothetical connection line 16 (cf. FIG. 2) connects the wave crests 18, the second hypothetical connection line 17 (cf. FIG. 2) connects the wave troughs 19. The three-dimensional roof shape formed between four adjacent bottom nodes 15 is made up of two triangles. The apex of these triangles can be placed, depending on the viewpoint, between the two wave crests 18 of the four adjacent bottom nodes 15 (then the roof is closed towards the sieve basket interior 6) or between the two wave troughs 19 of the four adjacent bottom nodes 15 (then the roof is open towards the sieve basket interior 6 and closed towards the sieve basket exterior 7).

FIG. 4 shows that the surface formed by the apertures 2, which shows a rectangular grid structure in the projected plan view from FIG. 2, has a high degree of three-dimensionality in perspective, which reduces the tendency to moisten this surface with droplets after removal from the CDD. In addition, the structure created by the corrugations 5 provides sufficiently large contact and fixation surfaces 14.

FIG. 5 shows the three-dimensional corrugations 5 as well as the fluting caused by them in a further section. There are so many corrugations 5 arranged over the entire surface of the bottom 3 that the total number of wave crests 18 and wave troughs 19 gives the user the impression of a flat surface. According to the invention, the advantages of a flat surface (such as the unproblematic placement of the sieve basket) are thus realized while avoiding its disadvantages (see above).

FIG. 6 shows a section of a sieve basket 1. Several items 20, in the present case surgical scissors, are arranged in this basket, which remain in position due to the corrugations 5 and due to the contact and fixation surfaces 14 created by them. The sieve basket 1 has side walls 4 in addition to the bottom 3. These also have apertures 21, which may differ geometrically from those in the bottom 3. In the present case, the apertures 21 are more finely meshed than the apertures 2, so that in such a case, in which the items 20 slide towards the side wall, there is no danger of pointed sections of the items 20 projecting sideways. Furthermore, the side walls 4 may be designed to be smooth, i.e. explicitly not corrugated.

The invention claimed is:

1. A sieve basket for receiving medical items to be disinfected or sterilized, the sieve basket comprising a bottom having a plurality of apertures and a base plane bounded by side walls,
   the bottom being a sheet metal part comprising periodic corrugations or indentations/bulges projecting from the base plane towards a sieve basket interior and/or towards a sieve basket exterior so that the bottom is given a meshwork surface structure, wherein
   the bottom is constructed from a plurality of longitudinal struts running in parallel in the base plane and a plurality of transverse struts running in parallel in the base plane,
   the plurality of longitudinal struts and the plurality of transverse struts running perpendicular to each other in the base plane, and
   the plurality of longitudinal struts and the plurality of transverse struts undulate up and down in a wave form over the entire bottom with an exception of a transition section in an area of the side walls, in order to form the periodic corrugations or indentations/bulges, and wherein
   the apertures, viewed in the base plane, have a rectangular shape and, by means of the corrugations or indentations/bulges, form a three-dimensional roof shape of two triangles towards the sieve basket interior and/or the sieve basket exterior.

2. The sieve basket according to claim 1, wherein the bottom is constructed from a plurality of longitudinal strut pairs, each formed by two longitudinal struts, and a plurality of transverse strut pairs, each formed by two transverse struts.

3. The sieve basket according to claim 1, wherein the two triangles are each formed in a plane and the planes have mutually opposed slopes.

4. The sieve basket according to claim 2, wherein the wave forms of the two struts of a strut pair run complementarily to each other, so that at a longitudinal or transverse position where one strut of the strut pair has a wave crest, the other strut of the strut pair has a wave trough so that the corrugations or indentations/bulges are evenly distributed over the bottom in its entirety.

5. The sieve basket according to claim 1, wherein the side walls also have apertures which differ in shape and size from the apertures of the bottom.

6. The sieve basket according to claim 2, wherein the struts of the longitudinal strut pairs and transverse strut pairs intersect in bottom nodes distributed in a grid structure in the base plane, wherein a sheet material depth of a bottom node corresponds to a sheet material depth of the struts.

7. The sieve basket according to claim 6, wherein a part of the bottom nodes is arranged projecting towards the sieve basket interior and another part of the bottom nodes is arranged projecting towards the sieve basket exterior.

8. The sieve basket according to claim 7, wherein a hypothetical connection line of the bottom nodes projecting towards the sieve basket interior runs diagonally to the grid structure and runs at right angles to a hypothetical connection line of the bottom nodes projecting towards the sieve basket exterior.

9. The sieve basket according to claim 3, wherein the three-dimensional roof shape created by the corrugations or indentations/bulges forms contact and fixation surfaces for items to be inserted into the sieve basket.

10. The sieve basket according to claim 1, wherein the plurality of longitudinal struts and the plurality of transverse struts intersect in bottom nodes either forming a wave crest or a wave trough, and the entirety of wave crests comprised in the bottom are arranged in a first plane, and the entirety of wave troughs comprised in the bottom are arranged in a second plane parallel to the first plane.

11. The sieve basket according to claim 10, wherein each of the plurality of longitudinal struts and the plurality of transverse struts has a sinusoidal shape or a cosine shape, so that there are no corrugations or indentations/bulges formed in a macro range but only corrugations or indentations/bulges formed in a micro range.

12. The sieve basket according to claim 1, wherein the bottom is given a meshwork surface structure without being woven.

* * * * *